US006280388B1

(12) United States Patent
Koger et al.

(10) Patent No.: US 6,280,388 B1
(45) Date of Patent: Aug. 28, 2001

(54) AEROGEL BACKED ULTRASOUND TRANSDUCER

(75) Inventors: James D. Koger, Santa Cruz, CA (US); Isaac Ostrovsky, Wellesley, MA (US)

(73) Assignee: Boston Scientific Technology, Inc., Maple Grove, MN (US)

( * ) Notice: Subject to any disclaimer, the term of this patent is extended or adjusted under 35 U.S.C. 154(b) by 0 days.

(21) Appl. No.: 09/050,543

(22) Filed: Mar. 30, 1998

Related U.S. Application Data

(63) Continuation-in-part of application No. 08/972,962, filed on Nov. 19, 1997, now Pat. No. 6,106,474.

(51) Int. Cl.[7] ........ A61B 8/14

(52) U.S. Cl. ........ 600/459

(58) Field of Search ........ 600/459, 463, 600/466, 467; 604/53, 96, 99–103; 29/25.35

(56) References Cited

U.S. PATENT DOCUMENTS 4,773,140 * 9/1988 McAusland ........ 29/25.35
5,311,095 * 5/1994 Smith et al. ........ 310/334
5,749,848 * 5/1998 Jang et al. ........ 604/53
5,785,040 * 7/1998 Axelgaard ........ 600/391
5,984,871 * 11/1999 TenHoff et al. ........ 600/459

* cited by examiner

*Primary Examiner*—Francis J. Jaworski
*Assistant Examiner*—Ali M. Imam
(74) *Attorney, Agent, or Firm*—Lyon & Lyon LLP

(57) ABSTRACT

An ultrasound transducer having an acoustic backing layer made of an aerogel material is disclosed. The ultrasound transducer comprises an acoustic element for transmitting and receiving ultrasound waves. An aerogel acoustic backing layer is bonded to the back side of the acoustic element. A matching layer may be attached to the front side of the acoustic element. The ultrasound transducer may be electrically connected using electrodes directly connected to the acoustic element. Alternatively, the aerogel acoustic backing may be coated with a metalized layer or doped so that it is electrically conductive. Then, the electrodes may be connected directly to the aerogel acoustic backing.

19 Claims, 6 Drawing Sheets

AEROGEL BACKED ULTRASOUND TRANSDUCER

This is a continuation-in-part of U.S. application Ser. No. 08/972,962, filed on Nov. 19, 1997 now U.S. Pat. No. 6,106,474. The priority of the prior application is expressly claimed, and the disclosure of the prior application is hereby incorporated by reference in its entirety.

FIELD OF THE INVENTION

The present invention relates to ultrasound transducers, and more specifically to an aerogel backed ultrasound transducer.

BACKGROUND OF THE INVENTION

Generally, ultrasound transducers are used in ultrasound imaging devices for imaging in a wide variety of applications, especially medical diagnosis and treatment. Ultrasound imaging devices typically employ mechanisms to transmit scanning beams of pulsed ultrasound energy and to receive the reflected echoes from each scan. The detected echoes are used to generate an image which can be displayed, for example, on a monitor.

A typical ultrasound transducer comprises an acoustic element which transmits and receives ultrasound waves. The acoustic element may be made of a piezoelectric or piezostrictive material, for example. The acoustic element has a front side from which ultrasonic waves are transmitted and received, and a back side which may be bonded to an acoustic backing layer. An acoustic backing layer dampens the acoustic element to shorten the pulse length, and ring-down and to allow the transmission and reception in one direction. To produce this effect, the acoustic backing layer is typically made of a material having an attenuative nature. Hence, conventional materials used as a backing layer have been dense materials such as tungsten and epoxy.

A significant drawback to using a dense backing layer material is that a large amount of power consumed by the acoustic element is lost in the backing layer rather than being used to transmit ultrasound waves. If 3 dB of the transducer signal is attenuated on the backing material, the equivalent of half the power drawn by the acoustic element is lost. In other words, if the transmission efficiency of the ultrasound transducer is increased by 3 dB, the power needed to drive the transducer can be cut in half for the same signal output.

In order to reduce the amount of power lost in the backing layer, transducers having air backing layers have been used. An air backing layer reflects almost all of the power directed out of the back side of the acoustic element toward the front side of the acoustic element. This occurs because of the large acoustic impedance mismatch between the air and the acoustic element.

There are several significant disadvantages associated with an air back transducer. One is that an air-backed transducer has a longer pulse length than a transducer having a dense backing layer. It is also very difficult to support an acoustic element in air.

Therefore, there is a need for an improved ultrasound transducer which provides effective damping of the acoustic element to reduce pulse length, electrically insulates and supports the ultrasound transducer, and reduces the amount of power lost in the backing layer.

SUMMARY OF THE INVENTION

The present invention provides an ultrasound transducer employing aerogel as a backing material. Aerogels are solids with extremely porous structures. Aerogels are produced by drying wet gels while retaining the spatial structure of the solid which originally contained water or solvent. Aerogels are discussed generally in "Resource Report: Jet Propulsion Laboratory," *NASA TechBriefs*, Vol. 19, No. 5, May 1995, at 8, 14. The properties and production of aerogels are described in detail in European Patent No. EP 0 640 564 A1 to Gerlach et al. Gerlach et al. suggests aerogels for use as acoustic matching layers on ultrasonic transducers. These and all other references cited herein are expressly incorporated by reference as if fully set forth in their entirety herein.

Aerogels have the lowest known density of all solid materials. Aerogels have densities as low as 0.015 g/cm$^3$. Aerogels also have sufficient strength to provide support structure for the acoustic element. In addition, aerogels provide excellent electrical isolation from the rest of the structure.

The ultrasound transducer of the present invention comprises a conventional acoustic element. For instance, the acoustic element may be a piezoelectric or piezostrictive material. An acoustic backing material made of an aerogel material is attached to a back side of the acoustic element.

Before attaching the aerogel backing material to the acoustic element, the aerogel backing material may be coated with a metalized layer so that it is electrically conductive. This allows at least one of the electrical connections to the transducer to be made to the backing material. Otherwise, electrodes must be attached directly to the acoustic element which is a more difficult assembly.

The extremely low density aerogel has a lower acoustic impedance than conventional backing materials, such as tungsten and epoxy, and a lower acoustic impedance than the acoustic element. The acoustic impedance of aerogel approximates the acoustic impedance of air. The mismatch of acoustic impedance between the aerogel backing material and the acoustic element causes ultrasound waves to reflect back towards the front side of the transducer. Therefore, the aerogel backing material provides a transducer with a higher signal output than a transducer employing conventional backing materials. The thickness of the acoustic element is sized such that the reflected ultrasound wave is in phase and additive to the ultrasound wave initially directed toward the front side of the transducer.

The electrical insulating quality of the aerogel provides exceptionally high electrical resistance. The acoustic properties of aerogel isolate the element and increase the transducer's output. Increasing the transducer signal increases signal-to-noise ratio and improves the displayed image.

A matching layer may be attached to the front side of the acoustic element. The matching layer is typically ¼ wavelength thick. The acoustic matching layer can be tuned to shorten the pulse length, yet transmit most of the transducer power through the matching layer. The reduction of the pulse length improves axial resolution for imaging.

DETAILED DESCRIPTION OF THE INVENTION

Figure 1:
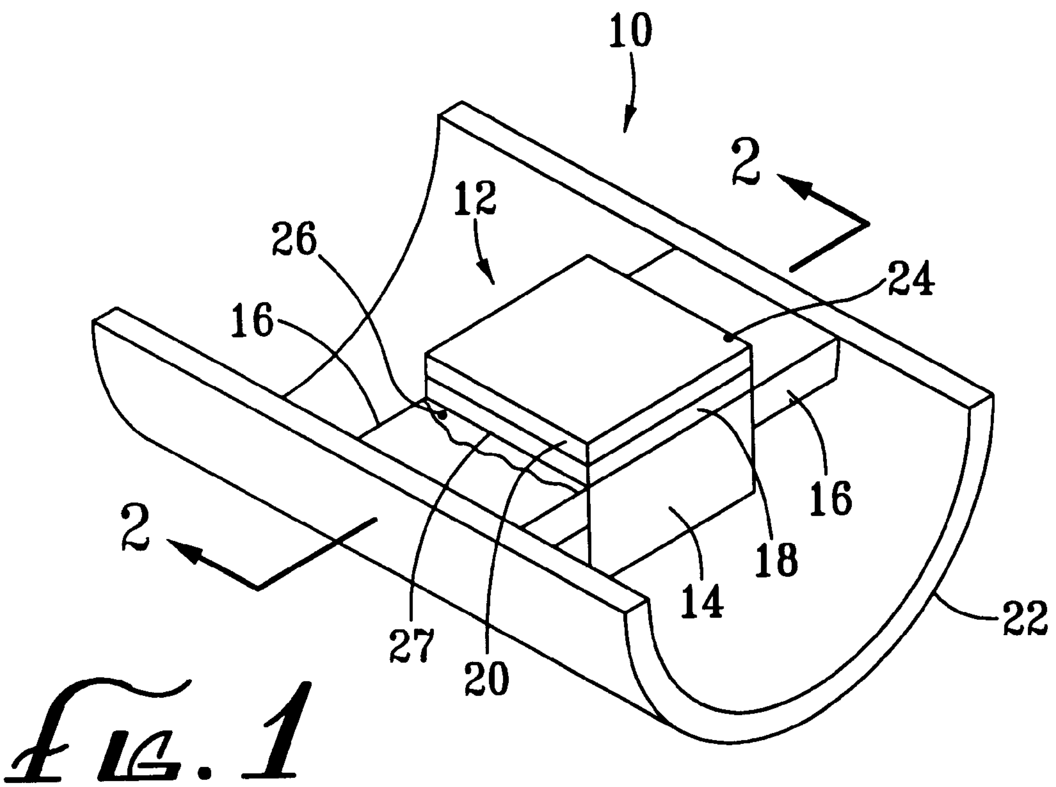
FIG. 1 is a perspective view of an ultrasound transducer in accordance with the present invention.

Referring to FIG. 1, an ultrasound transducer 12 according to the present invention is depicted. The ultrasound transducer 12 comprises an acoustic element 18. The acoustic element 18 may be a piezoelectric, piezostrictive or other suitable material depending on the transducer application. The selection of the material of the acoustic element 18 is a design choice which is well known in the art. An acoustic backing 14 made of an aerogel material is attached to a back side of the acoustic element 18.

Figure 2:
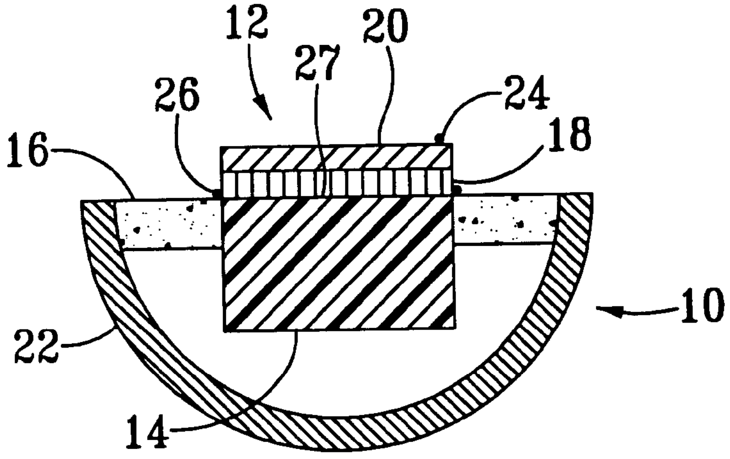
FIG. 2 is a cross-sectional view of the ultrasound transducer of FIG. 1.

An acoustic matching layer 20 may be attached to, or formed on, the front side of the acoustic element 18. The proper acoustic impedance and thickness of the acoustic matching layer 20 depends upon the environment or medium in which the ultrasound transducer 12 is used and the properties of the object to be imaged. The acoustic matching layer 20 may also be tuned to reduce pulse length while at the same time transmitting most of the power through the matching layer 20. The proper design of these parameters is known in the art. The acoustic matching layer 20 may be flat as shown in FIGS. 1 and 2, or alternatively may be curved to act as a lens to focus the ultrasound transducer 12.

For installing the ultrasound transducer 12 into an imaging device such as an imaging catheter, the ultrasound transducer 12 is mounted in a housing or support structure 22. The support structure 22 may be a semi-cylinder as shown in FIGS. 1 and 2 so that it is easily fitted into a tubular catheter or other lumen. The shape of the support structure 22 may be changed to match any particular application of the ultrasound transducer 12. The ultrasound transducer 12 may be attached to the support structure 22 using an insulating adhesive 16 such as epoxy. Alternative attachment methods may include welding, soldering, or conductive epoxies.

The ultrasound transducer 12 may be electrically connected using electrodes 24 and 26 directly connected to the acoustic element 18. Alternatively, the aerogel acoustic backing 14 may be coated with a metalized layer 27 or doped so that it is electrically conductive. Then, at least one of the electrodes may be connected to the aerogel acoustic backing 14.

The effectiveness of an aerogel acoustic backing 14 may be analyzed by considering it as an approximation of an air backing material. This approximation is supported by the following comparisons. The acoustic impedance of a material is defined as the density of the material multiplied by the speed of sound through the material, or:

$$\text{acoustic impedance}=Z=\text{density}\times\text{velocity}_{(sound\ in\ the\ material)}$$

The densities of the relevant materials are:

| | |
|---|---|
| aerogel | 15 kg/m$^3$ |
| air (20° C.) | 1.2 kg/m$^3$ |
| common piezoelectric material (PZT) | 7500–7800 kg/m$^3$ |

Comparing these densities, it can be seen that the density of aerogel is about a factor of 10 greater than air, and PZT is 500 times denser than aerogel. Because aerogel is closer to air in density than any known solid material, and because the speed of sound through a material tends to decrease with decreasing density, the acoustic impedance of aerogel may be assumed to approximate the acoustic impedance of air.

For comparison purposes, a transducer backed with a conventional backing material having an acoustic impedance of 10 megarayles will be examined (10 megarayles is within the range of acoustic impedance for many conventional backing materials). Assuming an acoustic element consisting of the piezoelectric lead zirconium titanate material (PZT) having an acoustic impedance of 33.7 megarayles, then the mismatch in acoustic impedance between the acoustic element and the backing is:

$$\frac{Z_{PZT}-Z_{backing}}{Z_{PZT}+Z_{backing}}=\frac{33.7-10}{33.7+10}=.547$$

Air has an acoustic impedance at 20° C. of 0.000411 megarayles. Then, the mismatch in acoustic impedance between the acoustic element and an air backing material is:

$$\frac{Z_{PZT}-Z_{air}}{Z_{PZT}+Z_{air}}=\frac{33.7-0.000411}{33.7+0.000411}\approx\frac{33.7}{33.7}=1$$

From the above equation, it can be seen that, even if the acoustic impedance of aerogel is greater than that of air by a factor of 10, the mismatch in acoustic impedance between the PZT and an aerogel backing material will be approximately 1. Now, comparing the aerogel (acoustic impedance approximated as air) backed transducer to the conventional material (acoustic impedance=10 megarayles) backed transducer, the difference in output may be represented as:

$$\log\frac{.547}{1}\times 20=5.3\text{ dB}$$

Therefore, the aerogel backed transducer results in approximately 5.3 dB higher output than the transducer having an acoustic backing material with an acoustic impedance of 10 megarayles.

Aerogel, therefore, ma y provide a thinner backing because it is using primarily the acoustic impedance mismatch to increase the transducer output. In other words, the interface between the transducer acoustic element 18 and the backing material 14 creates the output difference. The increased output of the transducer having an aerogel acoustic backing 14 allows a thinner layer of backing material than conventional materials. As a result, the transducer assembly 12 may be smaller.

For a given size and operating frequency, the transducer 12 can be configured to optimize the transducer's ringdown time, pulse length and bandwidth, peak amplitude, and center frequency. To optimize the transducer 12 having constant size and operating frequency, the thickness of the acoustic element 18, and the thickness 42 of the matching layer are varied until a transducer 12 is produced having the best combination of ringdown time, peak amplitude, center frequency, and bandwidth for the intended application. Utilizing an ultrasound piezoelectric transducer modeling software program entitled Piezocad Software from PiezoCad Co. of Woodinville, Wash., variously configured transducers 12 can be modeled on a computer. The following description of an iterative optimization of a transducer 12 according to the present invention is provided as an example, with the understanding that those skilled in the art could perform similar analysis to optimize transducers 12 of differing acoustic element materials, acoustic element 18 sizes, and operating frequencies.

The following analysis is performed by continuing to analyze the aerogel acoustic backing 14 as approximating an air backing material having an acoustic impedance of about 0.0004 megarayles.

For this analysis, the transducer 12 is assumed to have the following attributes: the acoustic element 18 material is lead zirconium titanate (PZT) having acoustic impedance of 33.7 megarayles (PZT 5A); the acoustic element is round and has a diameter of 0.0026"; the operating frequency is 30 megahertz (MHZ); and the matching layer 20 material is a silver epoxy having an acoustic impedance of 6.4 megarayles.

For each iteration of transducer 12, the variables are input into the piezocad program which produces a plot simulating the transducer 12 signal amplitude over a period of time, as shown in FIGS. 3–7.

Figure 3:
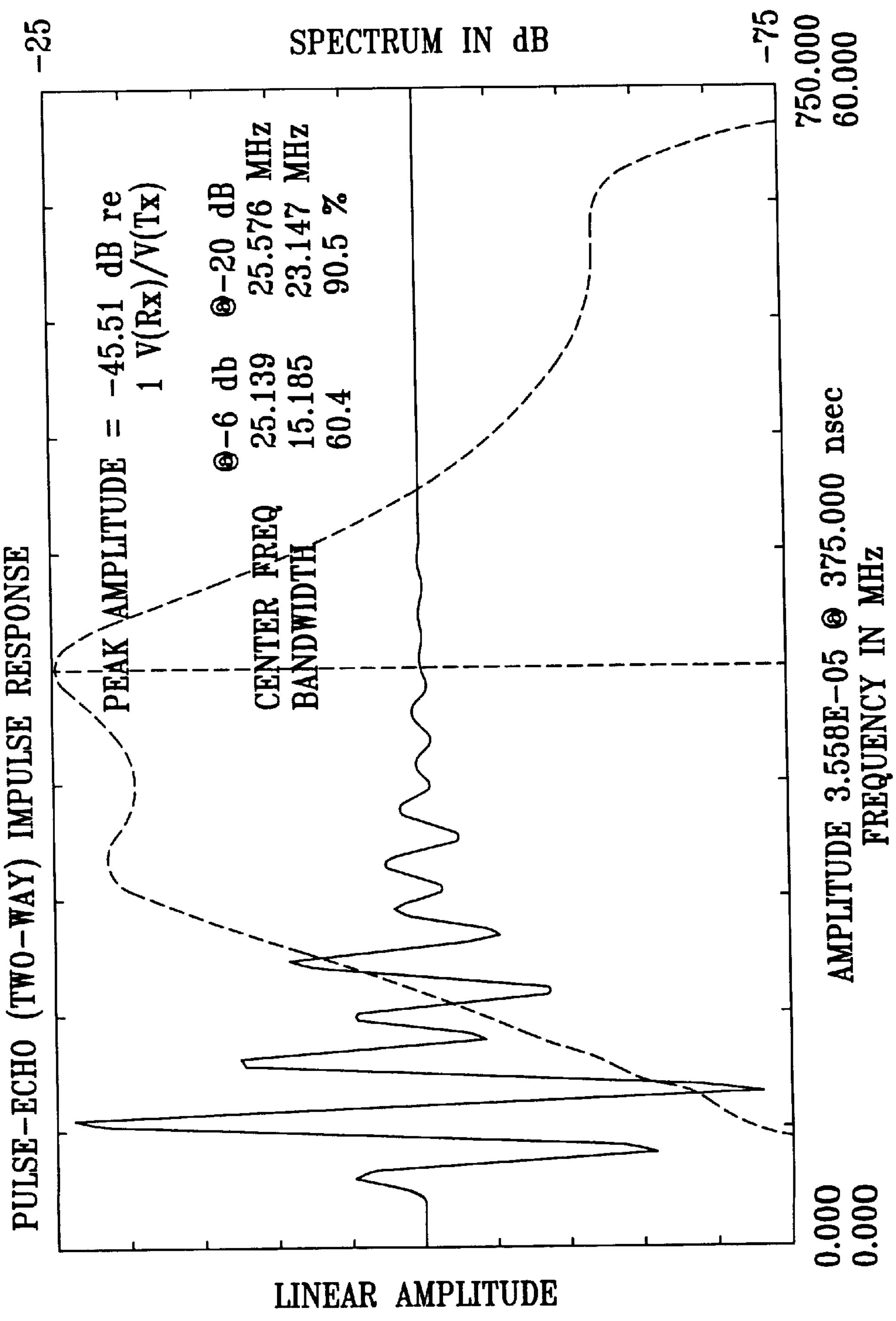
FIGS. 3–7 are signal plots of computer modeled ultrasound transducers.

FIG. 3 is a signal plot for a transducer 12 having a 0.0027" thick PZT and a 0.0010" thick matching layer 20. As the plot shows, the pulse length at −40 dB is 336.14 nanoseconds (nsec), the center frequency at −6 dB is 25.14 MHZ, the bandwidth at −6 dB is 15.19 MHZ, and the peak amplitude is −45.51 dB.

Figure 4:
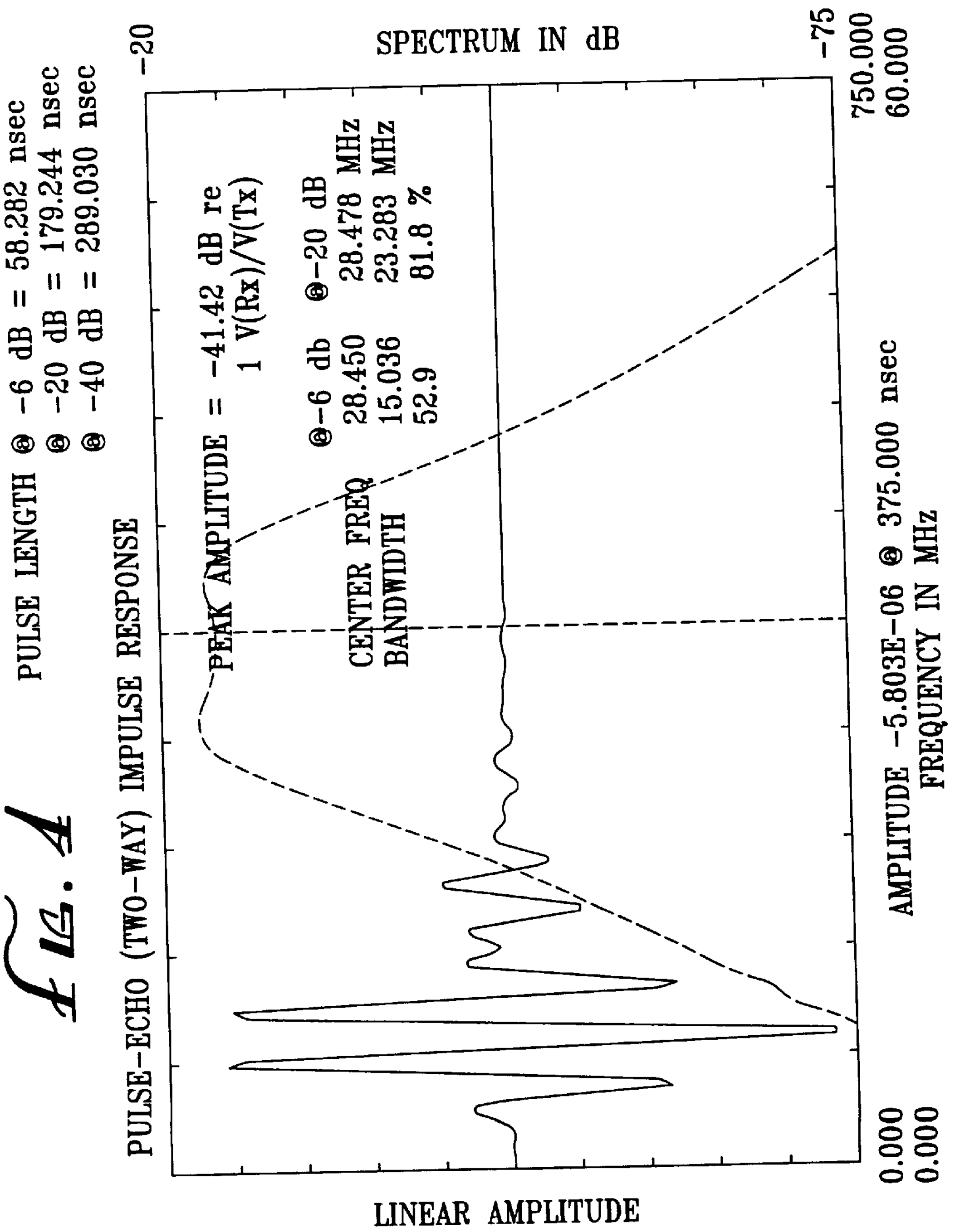

Turning now to FIG. 4, the PZT thickness is again 0.0027", but the matching layer 20 is 0.0007", slightly thinner than for the FIG. 3 model. Comparing the FIG. 4 model with the FIG. 3 model, it can be seen that the thinner matching layer 20 results in a shorter pulse length at −40 dB, a higher center frequency, a comparable bandwidth, and a higher peak amplitude. Hence, using a thinner matching layer 20 improved the operating characteristics of the transducer 12 from the FIG. 3 configuration to the FIG. 4 configuration.

Figure 5:
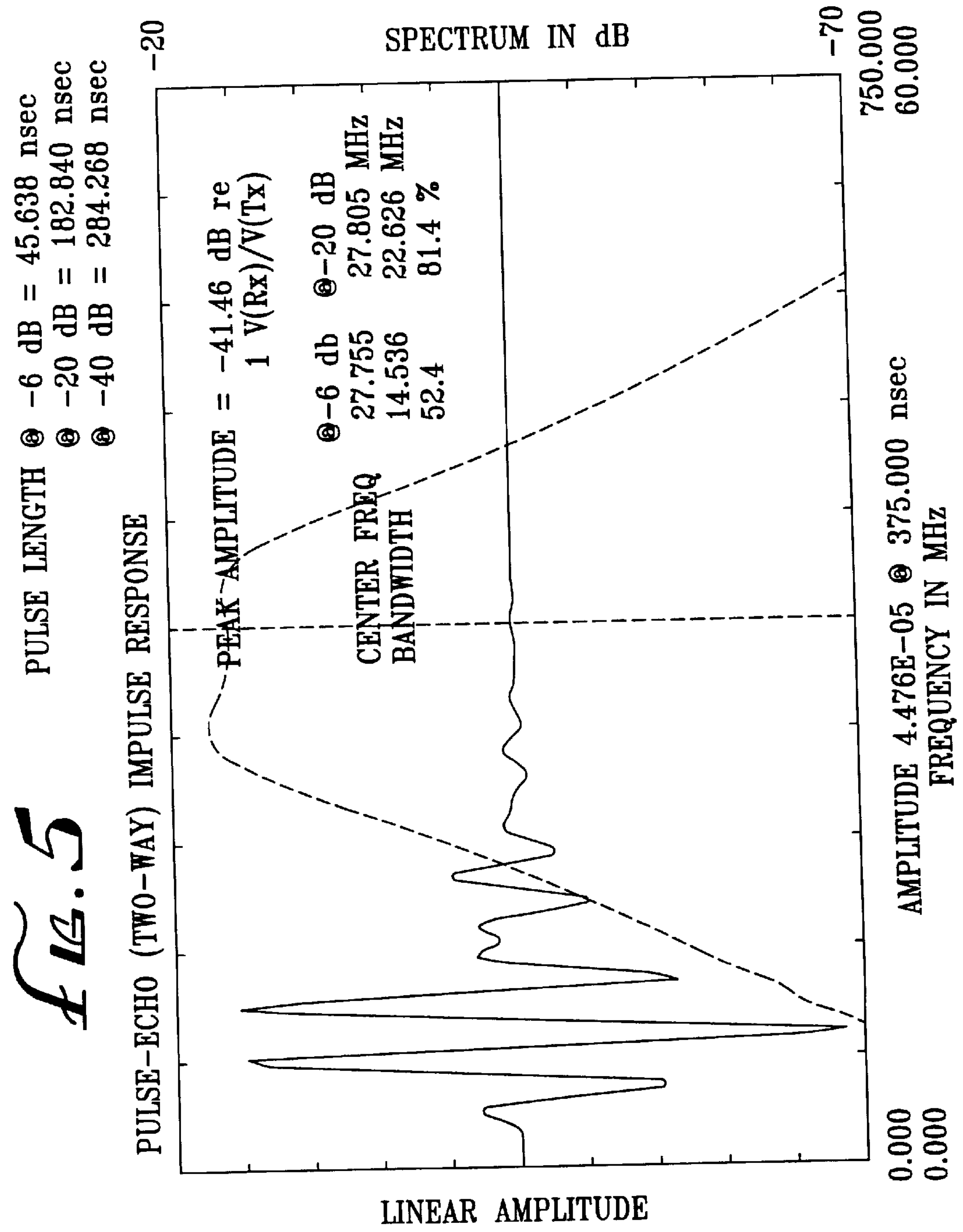

Now holding the matching layer thickness at 0.0007", the PZT thickness is increased to 0.0028" in the model of FIG. 5. The dimensions of the transducer of FIG. 5 are the dimensions of a transducer optimized for a heavy backing, but modeled here with an air backing. Compared to the FIG. 4 model, the FIG. 5 model has a decreased center frequency at −6 dB and at 20 dB, a decreased peak amplitude, and a decreased bandwidth. While the FIG. 5 model also has a shorter pulse length at −40 dB, it has a longer pulse length at −20 dB. Therefore, increasing the PZT thickness resulted in a transducer 12 having slightly worse operating characteristics, i.e., the 0.0027" PZT was better than the 0.0028" PZT.

Figure 6:
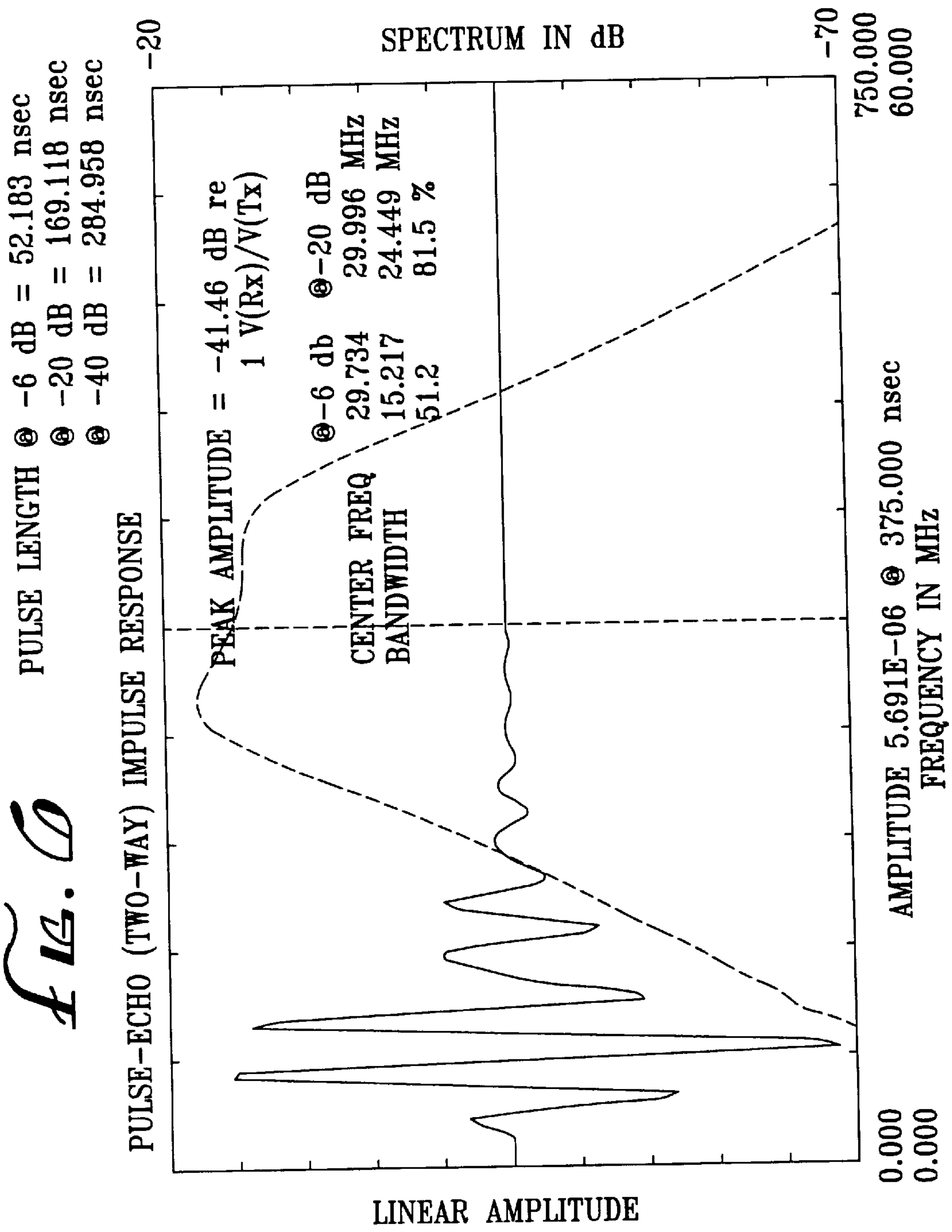

Returning now to a 0.002" PZT, the matching layer 20 thickness is set at 0.0006" in the model of FIG. 6. Comparing the FIG. 6 model to the FIG. 4 model, it is seen that the thinner matching layer 20 of FIG. 6 resulted in a higher center frequency, a shorter pulse length at all levels, but a slightly lower peak amplitude.

Figure 7:
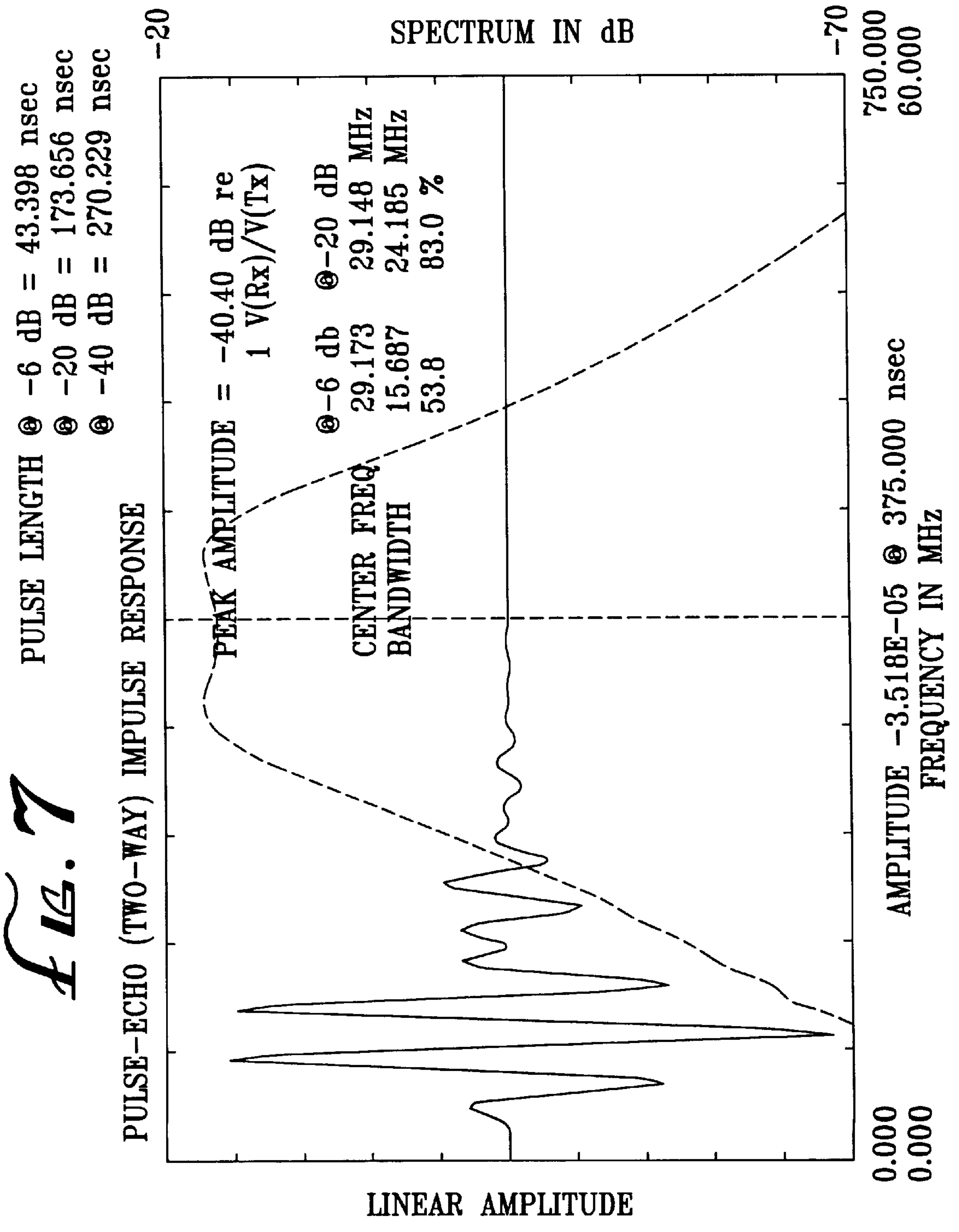

The next and final iteration of modeling the transducer 12 on the Piezocad Software is shown in FIG. 7. The PZT thickness is 0.0026", and the matching layer thickness is 0.0007". The FIG. 7 model, in almost all characteristics, is better than the FIGS. 5 and 6 models. The peak amplitude is higher, the center frequency is higher, and the pulse length is shorter at −40 dB. The bandwidth of the FIG. 7 model is slightly larger which will result in a transducer 12 having a slightly better axial resolution. All in all, the FIG. 7 model probably has the best overall operating characteristics and, therefore, has the optimized PZT and matching layer thicknesses for a 0.026" diameter transducer operating at 30 MHZ and using the materials having the properties listed above.

In the optimized air-backed transducer model of FIG. 7, we have overcome some of the disadvantages of air-backed transducers. The pulse length of the transducer has been reduced, and the bandwidth and pulse amplitude have been increased. This has been accomplished by slightly reducing the thickness of the PZT as used in the heavy acoustic backing type transducer of FIG. 5. The acoustic matching layer thickness of FIG. 5 remains unchanged in FIG. 7.

We have effectively constructed a band-pass filter to pass only desirable frequencies and block undesirable frequency elements. Decreasing the thickness of the PZT raises the emitted frequency spectrum of the element. By increasing the frequency spectrum of the PZT, we are effectively reducing the lower frequency component of the spectrum of frequencies emitted by the transducer. The lower frequency components of the emitted spectrum increase the pulse length. The matching layer thickness of FIG. 7 compared to FIG. 5 is unchanged, and so the higher spectrum of frequencies emitted because of the reduction in PZT thickness is filtered by the unchanged matching layer.

Thus, the reader will see that the present invention provides an improved ultrasound transducer. While the above description contains many specificities, these should not be construed as limitations on the scope of the invention, but rather as examples of particular embodiments thereof. Many other variations are possible.

Accordingly, the scope of the present invention should be determined not by the embodiments illustrated above, but by the appended claims and their legal equivalents.

What is claimed is:

1. An ultrasound transducer comprising:
- an acoustic element for transmitting and receiving ultrasound waves; and
- an acoustic backing material attached to a back side of said acoustic element, said acoustic backing layer made of a nonconductive aerogel material.

2. The ultrasound transducer of claim 1 wherein said acoustic unit includes a matching layer attached to a front side of said acoustic element.

3. The ultrasound transducer of claim 2 wherein said matching layer has a thickness of about 0.0006" to 0.0008".

4. The ultrasound transducer of claim 1 wherein the acoustic element is a piezoelectric material.

5. The ultrasound transducer of claim 1 wherein said acoustic element is a piezostrictive material.

6. The ultrasound transducer of claim 1 further comprising electronic leads operatively coupled to the acoustic element.

7. The ultrasound transducer of claim 6 wherein the leads are coaxial.

8. The ultrasound transducer of claim 6 wherein the leads are attached to the acoustic element.

9. The ultrasound transducer of claim 6 wherein said aerogel backing material is coated with a conductive material.

10. The ultrasound transducer of claim 9 wherein at least one of said electronic leads are attached to the backing material.

11. The ultrasound transducer of claim 1 wherein said acoustic element has a thickness of about 0.0026" to 0.0028".

12. The ultrasound transducer of claim 11 wherein said matching layer has a thickness of about 0.0006" to 0.0008".

13. The ultrasound transducer of claim 1, wherein said ultrasound transducer is positionable within an intravascular ultrasound imaging catheter, said intravascular ultrasound imaging catheter comprising a flexible elongate tubular member having a proximal end, a distal end, and a lumen therebetween, said ultrasound transducer being disposed within said distal end of said flexible elongate tubular member.

14. The ultrasound transducer of claim 1, wherein the ultrasound transducer is disposed within an imaging guidewire.

15. An ultrasound transducer comprising:
- an acoustic element for transmitting and receiving ultrasound waves;
- an acoustic backing material attached to a back side of said acoustic element, said acoustic backing layer made of a nonconductive aerogel material, and a matching layer attached to a front side of said acoustic element; and wherein said acoustic element is configured to emit a higher frequency spectrum than an acoustic element optimized for a heavy acoustic backing material.

16. The ultrasound transducer of claim 15 wherein the acoustic element is a piezoelectric material.

17. The ultrasound transducer of claim 15 wherein said acoustic element is a piezostrictive material.

18. The ultrasound transducer of claim 16 wherein said acoustic element has a reduced thickness compared to an acoustic element optimized for a heavy acoustic backing material.

19. The ultrasound transducer of claim 17 wherein said acoustic element has a reduced thickness compared to an acoustic element optimized for a heavy acoustic backing material.

* * * * *